US010912482B2

(12) United States Patent
Bozsak et al.

(10) Patent No.: US 10,912,482 B2
(45) Date of Patent: Feb. 9, 2021

(54) METHOD FOR DETERMINING AT LEAST ONE TYPE AND/OR CONDITION OF CELLS AND SYSTEM

(71) Applicants: Ecole Normale Superieure de Cachan, Cachan (FR); Sensome SAS, Paris (FR); Ecole Polytechnique, Paris (FR); Centre National de la Recherche Scientifique, Paris (FR)

(72) Inventors: Franz Bozsak, Versailles (FR); Abdul Barakat, Gif-sur-Yvette (FR); Pierluca Messina, Paris (FR); Olivier Francais, Melun (FR); Bruno Carreel, Paris (FR); Bruno Le Pioufle, Paris (FR); Myline Cottance, Paris (FR)

(73) Assignee: Sensome SAS, Massy (FR)

( * ) Notice: Subject to any disclaimer, the term of this patent is extended or adjusted under 35 U.S.C. 154(b) by 343 days.

(21) Appl. No.: 15/769,968

(22) PCT Filed: Oct. 21, 2016

(86) PCT No.: PCT/EP2016/075456
§ 371 (c)(1),
(2) Date: Apr. 20, 2018

(87) PCT Pub. No.: WO2017/068157
PCT Pub. Date: Apr. 27, 2017

(65) Prior Publication Data
US 2018/0303372 A1 Oct. 25, 2018

(30) Foreign Application Priority Data

Oct. 23, 2015 (FR) .................................. 15 60174

(51) Int. Cl.
*A61B 5/00* (2006.01)
*A61B 5/053* (2021.01)
(Continued)

(52) U.S. Cl.
CPC ............ *A61B 5/053* (2013.01); *A61B 5/0031* (2013.01); *A61B 5/0537* (2013.01);
(Continued)

(58) Field of Classification Search
CPC ..... A61B 5/053; A61B 5/0537; A61B 5/0538; A61B 5/0031; A61B 5/4851
See application file for complete search history.

(56) References Cited

U.S. PATENT DOCUMENTS 5,447,529 A    9/1995 Marchlinksi et al.
5,800,350 A    9/1998 Coppleson et al.
(Continued)

FOREIGN PATENT DOCUMENTS

AU    4755602 A    12/2002
CN    1353619 A    6/2002
(Continued)

OTHER PUBLICATIONS

Arndt et al., Bioelectrical impedance assay to monitor changes in cell shape during apoptosis. Biosensors and Bioelectronics. 2004;19:583-94.
(Continued)

*Primary Examiner* — Max F Hindenburg
(74) *Attorney, Agent, or Firm* — Wolf, Greenfield & Sacks, P.C.

(57) ABSTRACT

The invention relates to a method for discriminating cells of a cellular structure, notably of a cellular tissue, comprising the steps consisting in determining (12) a frequency spectrum of the impedance of the cellular structure; defining (22) at least one model of the impedance of the cellular structure including a constant phase element (30); determining (44) the impedance of the constant phase element (30) which optimizes the correlation of each model of the impedance of the cellular structure with the spectrum; and deducing (66),
(Continued)

from the impedance of the constant phase element (30) or from the impedances of the constant phase elements (30), an item of information on the cells of the cellular structure. The invention also relates to a system for implementing the method for discriminating cells of a cellular structure.

22 Claims, 9 Drawing Sheets

(51) Int. Cl.
    *A61B 5/0537*     (2021.01)
    *A61B 5/0538*     (2021.01)
    *C12Q 1/04*     (2006.01)

(52) U.S. Cl.
    CPC .......... *A61B 5/0538* (2013.01); *A61B 5/4851* (2013.01); *A61B 5/686* (2013.01); *A61B 5/6847* (2013.01); *A61B 5/6851* (2013.01); *A61B 5/6852* (2013.01); *A61B 5/6862* (2013.01); *C12Q 1/04* (2013.01); *A61B 2562/0214* (2013.01)

(56) References Cited

U.S. PATENT DOCUMENTS

| | | |
|---|---|---|
| 5,938,624 A | 8/1999 | Akerfeldt et al. |
| 6,063,028 A | 5/2000 | Luciano |
| 6,090,052 A | 7/2000 | Akerfeldt et al. |
| 6,106,486 A | 8/2000 | Tenerz et al. |
| 6,112,598 A | 9/2000 | Tenerz et al. |
| 6,206,835 B1 | 3/2001 | Spillman, Jr. et al. |
| 6,428,336 B1 | 8/2002 | Akerfeldt |
| 6,437,551 B1 | 8/2002 | Krulevitch et al. |
| 6,461,301 B2 | 10/2002 | Smith |
| 6,679,269 B2 | 1/2004 | Swanson |
| 8,277,386 B2 | 10/2012 | Ahmed et al. |
| 8,491,567 B2 | 7/2013 | Magnin et al. |
| 8,777,898 B2 | 7/2014 | Suon et al. |
| 8,840,560 B2 | 9/2014 | Hossack et al. |
| 9,121,806 B1 | 9/2015 | Bhansali et al. |
| 9,301,699 B2 | 4/2016 | Hubinette et al. |
| 2002/0043113 A1 | 4/2002 | Tulkki et al. |
| 2002/0077627 A1 | 6/2002 | Johnson et al. |
| 2002/0177782 A1 | 11/2002 | Penner |
| 2005/0065592 A1 | 3/2005 | Holzer |
| 2006/0047205 A1 | 3/2006 | Ludomirsky et al. |
| 2006/0254600 A1 | 11/2006 | Danek et al. |
| 2007/0255145 A1 | 11/2007 | Smith et al. |
| 2007/0255270 A1 | 11/2007 | Carney |
| 2008/0262489 A1 | 10/2008 | Steinke |
| 2010/0191141 A1 | 7/2010 | Aberg |
| 2011/0054583 A1 | 3/2011 | Litt et al. |
| 2011/0251469 A1 | 10/2011 | Varadan |
| 2012/0016206 A1 | 1/2012 | Ramarajan et al. |
| 2012/0036689 A1 | 2/2012 | Sjosten et al. |
| 2012/0061257 A1 | 3/2012 | Yu et al. |
| 2012/0172731 A1 | 7/2012 | Smith |
| 2012/0190989 A1 | 7/2012 | Kaiser et al. |
| 2012/0316454 A1 | 12/2012 | Carter |
| 2013/0274712 A1 | 10/2013 | Schecter |
| 2013/0282084 A1 | 10/2013 | Mathur et al. |
| 2014/0005558 A1 | 1/2014 | Gregorich |
| 2014/0058197 A1 | 2/2014 | Salahieh et al. |
| 2014/0058275 A1 | 2/2014 | Gregorich et al. |
| 2014/0066790 A1 | 3/2014 | Burkett et al. |
| 2014/0066791 A1 | 3/2014 | Burkett |
| 2014/0081244 A1 | 3/2014 | Voeller et al. |
| 2014/0180031 A1 | 6/2014 | Anderson |
| 2014/0276109 A1 | 9/2014 | Gregorich |
| 2014/0276223 A1 | 9/2014 | Gustafsson |
| 2014/0284422 A1 | 9/2014 | Sapir |
| 2014/0343382 A1 | 11/2014 | Kersey et al. |
| 2015/0032011 A1 | 1/2015 | McGowan et al. |
| 2015/0051499 A1 | 2/2015 | McGowan |
| 2015/0209526 A1 | 7/2015 | Matsubara et al. |
| 2015/0297807 A1 | 10/2015 | Leblanc et al. |
| 2015/0313478 A1 | 11/2015 | Veszelei et al. |
| 2016/0051323 A1 | 2/2016 | Stigall et al. |
| 2016/0058382 A1 | 3/2016 | Burkett et al. |
| 2016/0058977 A1 | 3/2016 | Burkett et al. |
| 2016/0073957 A1 | 3/2016 | Szunyog |
| 2016/0121085 A1 | 5/2016 | Burkett et al. |
| 2016/0287178 A1 | 10/2016 | Ranganathan et al. |
| 2016/0303354 A1 | 10/2016 | Burkett et al. |
| 2019/0388002 A1 | 12/2019 | Bozsak et al. |

FOREIGN PATENT DOCUMENTS

| | | |
|---|---|---|
| CN | 1400462 A | 3/2003 |
| CN | 1504578 A | 6/2004 |
| CN | 102016575 A | 4/2011 |
| CN | 102973267 A | 3/2013 |
| DE | 101 03 503 A1 | 8/2002 |
| EP | 0904739 A | 3/1999 |
| EP | 2271933 B1 | 12/2012 |
| JP | 2004-517677 | 6/2004 |
| WO | WO 99/42176 A1 | 8/1999 |
| WO | WO 01/37726 A1 | 5/2001 |
| WO | WO 03/057011 A2 | 7/2003 |
| WO | WO 2006/113747 A2 | 10/2006 |
| WO | WO 2009/096821 A1 | 8/2009 |
| WO | WO 2009/103156 A1 | 8/2009 |
| WO | WO 2009/136157 A2 | 11/2009 |
| WO | WO 2016/050972 A1 | 4/2016 |

OTHER PUBLICATIONS

Brug et al., The Analysis of Electrode Impedances Complicated by the Presence of a Constant Phase Element. Journal of Electroanalytical Chemistry and Interfacial Electrochemistry. 1984;176:275-95.
Chauveau et al., Ex Vivo Discrimination between Normal and Pathological Tissues in Human Breast Surgical Biopsies Using Bioimpedance Spectroscopy. Annals of the New York Academy of Sciences. 1999;873:42-50.
Cho et al., Chip-based time-continuous monitoring of toxic effects on stem cell differentiation. Annals of Anatomy. 2009;191:145-52.
Cho et al., Electrical characterization of human mesenchymal stem cell growth on microelectrode. Microelectronic Engineering. Science Direct. 2008;85:1272-4.
Cho et al., Impedance monitoring of herpes simplex virus-induced cytopathic effect in Vero cells. Elsevier. Sensors and Actuators B. 2007;123:978-82.
Cole et al., Dispersion and Absorption in Dielectrics. Journal of Chemical Physics. 1941;9:341-51.
Franks et al., Impedance Characterization and Modeling of Electrodes for Biomedical Applications. Biomedical Engineering. IEEE Transactions on Biomedical Engineering. 2005;52(7):1295-1302.
Giaever et al., A morphological biosensor for mammalian cells. Nature. 1993;366:591-2.
Giaever et al., Micromotion of mammalian cells measured electrically. Proceedings of the National Academy of Sciences. 1991;88:7896-900.
Grimnes et al., Bioimpedance and Bioelectricity Basics. Academic. Elsevier. Second Edition. 2000. 484 pages.
Helen et al., Investigation of tissue bioimpedance using a macro-needle with a potential application in determination of needle-to-nerve proximity. Proceedings of the 8th International Conference on Sensing Technology. Sep. 2-4, 2014. 376-80.
Hilderbrandt et al., Detection of the osteogenic differentiation of mesenchymal stem cells in 2D and 3D cultures by electrochemical impedance spectroscopy. Journal of Biotechnology. 2010;148:83-90.
Hirschorn et al., Determination of effective capacitance and film thickness from constant-phase-element parameters. Electrochimica Acta. 2010;55:6218-27.
Linderholm et al., Two-dimensional impedance imaging of cell migration and epithelial stratification. Lab on a Chip. Paper. 2006;6:1155-62.

(56) References Cited

OTHER PUBLICATIONS

Luong et al., Monitoring Motility, Spreading, and Mortality of Adherent Insect Cells Using an Impedance Sensor. Analytical Chemistry. 2001;73:1844-8.
Orazem et al., Dielectric Properties of Materials Showing Constant-Phase-Element (CPE) Impedance Response. Journal of the Electrochemcial Society. 2013;160(6):C215-C225.
Orazem et al., Electrochemical Impedance Spectroscopy. John Wiley & Sons, Inc. 2008. 533 pages.
Pauly et al., Electrical Properties of Mitochondrial Membranes. The Journal of Biophysical and Biochemical Cytology. 1960;7(4):589-601.
Qiao et al., Bioimpedance Analysis for the Characterization of Breast Cancer Cells in Suspension. Biomedical Engineering. IEEE Transactions. 2012;59:2321-90.
Rigaud et al., In vitro tissue characterization and modelling using electrical impedance measurements in the 100 Hz-10 MHz frequency range. Physiological Measurement. 1995;16:A15-A28.
Schade-Kampmann et al., On-chip non-invasive and label-free cell discrimination by impedance spectroscopy. Cell Prolif. 2008;41:830. 40.
Xiao et al., Assessment of Cytotoxicity Using Electric Cell-Substrate Impedance Sensing: Concentration and Time Response Function Approach. Analytical Chemistry. 2002;74:5748-53.
French Communication for French Application No. 1459531 dated Oct. 3, 2014.
French Communication for French Application No. 1459531 dated Jun. 30, 2015.
International Search Report and Written Opinion for International Application No. PCT/EP2015/072859 dated Dec. 3, 2015.
International Preliminary Report on Patentability for International Application No. PCT/EP2015/072859 dated Apr. 13, 2017.
International Search Report and Written Opinion for International Application No. PCT/EP2016/075456 dated Dec. 9, 2016.
International Preliminary Report on Patentability for International Application No. PCT/EP2016/075456 dated May 3, 2018.
International Search Report and Written Opinion for International Application No. PCT/EP2017/058169 dated Jun. 21, 2017.
International Search Report and Written Opinion for International Application No. PCT/IB2017/001230 dated May 4, 2018.
International Search Report and Written Opinion for International Application No. PCT/EP2017/079960 dated Apr. 5, 2018.
[No Author Listed], Electronique et informatique. Daniel Robert. http://www.electronique-et-informatique.fr/anglais/Digit/Digit_8T. html Sep. 22, 2006. Last accessed Aug. 7, 2018. 9 pages.
[No Author Listed], Ring oscillator. https://en.wikipedia.org/w/index. php?title=Ring_oscillator&oldid=674008095 Aug. 1, 2015. Last accessed Aug. 7, 2018. 4 pages.
FR 1560174, Oct. 23, 2015, Written Opinion on Patentability.
FR 1560174, Jun. 17, 2016, Preliminary Search Report.
PCT/IB2017/001230, May 4, 2018, International Search Report and Written Opinion.
PCT/EP2017/079960, Apr. 5, 2018, International Search Report and Written Opinion.
PCT/EP2016/075456, Dec. 9, 2016, International Search Report and Written Opinion.
PCT/EP2016/075456, May 3, 2018, International Preliminary Report on Patentability.
European Communication for European Application No. 16785160.9 dated Sep. 16, 2019.
EP16785160.9, Sep. 16, 2016, European Communication.
Written Opinion on Patentability for French Application No. 1560174 dated Oct. 23, 2015.
Preliminary Search Report for French Application No. 1560174 dated Jun. 17, 2016.
Bilge et al., Label-Free Recognition of Drug Resistance via Impedimetric Screening of Breast Cancer Cells. Plos One. 2013;8(3). 12 pages.
Nguyen et al., A cell impedance sensor chip for cancer cells detection with single cell resolution. 2013 IEEE Sensors. Nov. 3, 2013. 1-4.
Srinivasaraghavan et al., Microelectrode bioimpedance analysis distinguishes basal and claudin-low subtypes of triple negative breast cancer cells. Biomedical Microdevices. 2015;17(4):1-11.
Xu et al., A review of impedance measurements of whole cells. Biosensors and Bioelectronics. Oct. 22, 2015. vol. 77. 824-836.
U.S. Appl. No. 16/092,872, filed Oct. 11, 2018, Bozsak et al.
FR 1459531, Oct. 3, 2014, Written Opinion on Patentability.
FR 1459531, Jun. 30, 2015, Preliminary Search Report.
PCT/EP2015/072859, Dec. 3, 2015, International Search Report and Written Opinion.
PCT/EP2015/072859, Apr. 13, 2017, International Preliminary Report on Patentability.
PCT/EP2017/058169, Jun. 2, 2017, International Search Report and Written Opinion.
U.S. Appl. No. 16/462,870, filed May 21, 2019, Lebedev et al.
Japanese Notice of Reasons for Rejection dated Oct. 20, 2020 in connection with Japanese Application No. 2018-540214.
Amemiya et al., Denkikagaku: Sokutei to Kaiseki no Tebiki Inpidansuhou (1). Electrochemistry, Electrochemistry society of japan. Apr. 5, 2006;74(4):351-357.
Chinese Office Action dated Nov. 27, 2020 in connection with Chinese Application No. 201680075555.X.
Li et al., Corrosion Test Method and Monitoring Technology. China Petrochemical Press. May 31, 2007:58-59.

METHOD FOR DETERMINING AT LEAST ONE TYPE AND/OR CONDITION OF CELLS AND SYSTEM

RELATED APPLICATIONS

This Application is a national stage filing under 35 U.S.C. 371 of International Patent Application Serial No. PCT/EP2016/075456, filed Oct. 21, 2016, titled "METHOD FOR DETERMINING AT LEAST ONE TYPE AND/OR CONDITION OF CELLS AND SYSTEM", which claims priority to French application number 1560174, filed Oct. 23, 2015.

Embodiments of the present invention relate to cell discrimination and to a method for determining at least one type and/or condition of cells and to a system for implementing this method.

Cell discrimination should be understood here to include the determination of information relating to the cells of a tissue or more generally of a cellular structure. The information relating to the cells may notably include the cell type or types present in the tissue and/or their condition, such as the condition of the cells included inflamed, cancerous or healthy, among others, and cancerous phases including hyperplasie phase, dysplasia phase, carcinoma in-situ phase, invasive carcinome phase, metastatic carnicome phase among others.

The determination of the type of cells present in a tissue may be, for example, useful in tracking the healing of the endothelium of an artery, after a stent has been fitted. It is known that the insertion of a stent may cause a wound to the endothelium of the artery. As a result of this wound, a scar tissue may be formed which may comprise endothelial cells, smooth muscular cells and platelets (or thrombocytes). The proliferation of some of these cells may provoke serious pathologies, such as restenosis or thrombosis. It is therefore particularly advantageous to be able to discriminate, notably in situ, the cells of the scar tissue.

Numerous devices and methods have already been proposed, aiming to determine the type of cells and/or the condition of cells of a cellular structure, notably in a tissue. These methods are usually based on a measurement of an impedance of the tissue or of the cells.

U.S. Pat. No. 6,437,551 describes a micro fluidic device for detecting and identifying cells. This microfluidic device comprises a microfluidic chip with at least one microconduit provided with electrodes, and an electrical circuit, linked to the electrodes, for detecting signals associated with particles passing through the microconduit. According to this document it is possible to compute from variations of the spectrum of the measured impedance a value of membrane capacitance of the cell and then differentiate cells according to this value. However, the thus determined membrane capacitance exhibits strong variations from one cell to another, even between two cells of a same type. This method therefore presents a limited degree of reliability and furthermore cannot be implemented in vivo.

EP-B-2 271 933 describes a method for characterizing cells or cellular structures. This method consists first of all in determining a normalized impedance of a sample to be tested, over a range of frequencies. The normalized impedance corresponds to the ratio between the impedance of the sample actually measured in the test system used, and an off-load impedance of the test system, without the sample to be tested. According to this method, the type of cells of the sample may then be determined as a function of the frequency or frequencies of one or more peaks of the normalized impedance. This method also presents a limited degree of reliability as the frequency of the peak or peaks may vary greatly from one measurement to another and from one test system to another. Furthermore, this method is difficult to implement in vivo because it requires an "off-load" measurement, with test conditions similar to the conditions encountered when the sample to be tested is present, which may prove difficult to achieve as blood properties may exhibit rapid and significant variations.

EP-B-2 271 933 also teaches that it is possible to determine an equivalent circuit for modelling the normalized impedance. In this case, conclusions may be drawn from values of a capacitance or of a resistance of the circuit, which are characteristic of an organism and/or of its stage of growth. This patent is silent about models that could be implemented in this context.

U.S. Pat. No. 9,121,806 describes an instrument for using impedance spectroscopy to monitor growth of cells outside of a body to determine whether the cells are cancerous. Equivalent circuit modelling is performed, with constant phase elements. The evolutions of Cell layer resistance and $CPE_{cell}$ are plotted versus time.

US2012/0316454 discloses a technique for using impedance spectroscopy to monitor the positioning of a cochlear implant within a human body, using electrodes to identify how close the implant is to tissues and what tissues the electrodes are near. This document describes performing equivalent circuit modelling, with the equivalent circuit model including a constant phase element. A curve is computed and compared to known curve patterns to identify the proximity of the electrodes to one or more tissue structures.

The article "A cell impedance sensor chip for cancer cells detection with single cell resolution" Tien Anh Nguyen et al, IMTEK, University of Freiburg, Freiburg, Germany, discloses a chip for high-resolution detection of cancer cells which uses impedance spectroscopy and circuit equivalent modelling, where the models employed include a constant phase element. Cell discrimination is based on the modification of membrane capacitance Cm of the equivalent model.

The article "A review of impedance measurements of whole cells" Youchun Xu et al Biosensors and Bioelectronic, 77 (2016) 824-836 describes various techniques for an impedance measurement with cells, including spectroscopy techniques that employ equivalent circuit modelling with constant phase elements. Various parameters are computed such as cell membrane capacitance $C_{mem}$.

The article "Determination of effective capacitance and film thickness from constant-phase-elements parameters" Bryan Hirschorn et al, Electrochimica Acta (2010) 6218-6227 discusses determination of effective capacitance from CPE parameters for two types of time-constant distributions, i.e. surface distributions and normal distributions. Applications to Faradaic reactions at electrode surface are disclosed. Effective capacitance of human skin is computed to try estimate skin thickness.

There is a need for methods and systems enabling determination with relative accuracy a type and/or condition of a cell, and that could operate for in vivo measurements if desired.

Exemplary embodiments of the present invention relate, according to a first aspect, to a method for determining at least one type and/or condition of cells of a cellular structure, the method comprising comparing at least one value representative of an effective capacitance $C_{eff}$ of the cellular structure to at least one reference value determined for at least one known type and/or condition of cells and determining based at least on this comparison at least one type and/or condition of cells of the cellular structure, the effective capacitance $C_{eff}$ being based on at least one equivalent circuit model of the impedance of the cellular structure including at least a first constant phase element having a pseudo-capacitance, the effective capacitance $C_{eff}$ being dependant at least on the pseudo-capacitance of the first constant phase element and on at least one electrical resistivity quantity of said equivalent circuit model.

$C_{eff}$ has dimensions of a capacitance and may be expressed as a power of the pseudo-capacitance of the first constant phase element times a power of the electrical resistivity quantity.

It has been found that the method according to some embodiments of the invention makes it possible to accurately differentiate different types of cells and/or different conditions of a same type of cell. The method is effective, accurate and fast. Furthermore, it may not require any calibration measurement. It may be implemented in vivo.

The value representative of the effective capacitance may be the effective capacitance itself of an image of the effective capacitance by a linear or non-linear function. This function may have for sole parameter the effective capacitance or involve other parameters, for even greater accuracy of the determination.

The method may comprise computing the value representative of the effective capacitance based on at least one impedance spectrum of the cellular structure. The impedance spectrum may be transformed for this computation, for example by some scaling, or a raw impedance spectrum may be used. When the impedance spectrum is transformed, the computation of the value representative of the effective capacitance takes into account the transformation carried out on the impedance spectrum.

The method may comprise determining parameters of the equivalent circuit model that best fit the impedance spectrum given a mathematical optimization method.

The method may comprise measuring the impedance spectrum. In other words, a same system may carry out the measurement and compute the value representative of the effective capacitance. In a variant, the system that computes the value representative of the effective capacitance is not the same as the one that makes the measurement. For example, the measurement is made by third parties and transmitted via a network to a server where the value representative of the effective capacitance is computed. The result of the determination may then be returned to the third parties.

The impedance spectrum may be measured in a frequency range from about $10^3$ Hz to $10^8$ Hz, and preferably in a frequency range from about $10^4$ Hz to $10^7$ Hz.

The method may comprise comparing at least one value representative of an effective capacitance of the cellular structure to a plurality of reference values determined for a plurality of known type of cells and determining based at least on this comparison at least one type of cells of the cellular structure.

The plurality of known cell types may comprise at least three cell types, for example endothelial cells, smooth muscle cells and blood platelets.

The method may comprise comparing at least one value representative of an effective capacitance of the cellular structure to a plurality of reference values determined for a plurality of known conditions of cells and determining based at least on this comparison at least one condition of cells of the cellular structure. The condition may be at least one of an inflamed condition, a cancerous condition, a healthy condition, and an undifferentiated or differentiated condition of stem cells and cancerous phases including hyperplasie phase, dysplasia phase carcinoma in-situ, invasive carcinome phase, metastatic carnicome phase, among others.

The frequency spectrum may be measured in vivo. In some exemplary embodiments, the frequency spectrum is determined in vivo in a mammal. The cellular structure may be present in a vicinity of a surgical device which is one of a stent, scaffold, graft, catheter, guidewire, probe, occlude device, heart valve, pacemaker, ICD stent.

In a variant, the frequency spectrum is measured in vitro.

The frequency spectrum is determined with at least two electrodes, but preferably at least four electrodes are used.

The first constant phase element is preferably a membrane constant phase element $CPE_m$ having an impedance in the form $$Z_{CPEm} = \frac{1}{(j\omega)^\alpha Q_0}$$

where $Q_0$ is the pseudo-capacitance of the constant phase element and $\alpha$ is a real number lying between 0 and 1, and wherein the effective capacitance $C_{eff}$ depends at least on $Q_0$ and $\alpha$.

The at least one value representative of the effective capacitance $C_{eff}$ of the cellular structure may be $C_{eff}/S$, where S is a total surface of electrodes for measuring an impedance spectrum based on which the effective capacitance is computed.

The at least one value representative of the effective capacitance $C_{eff}$ of the cellular structure may be $\log(C_{eff})$ or any other linear or non linear function.

The equivalent circuit model preferably comprises a second constant phase element being a double layer constant phase element $CPE_{dl}$.

The equivalent circuit model may comprise a shunt circuit constituted by the first constant phase element of impedance $$Z_{CPEm} = \frac{1}{(j\omega)^\alpha Q_0}$$

shunted by a resistor R2, and a resistor R1 in series with the shunt circuit.

Preferably, the equivalent circuit further comprises a second constant phase element in series with the resistor R1.

The effective capacitance $C_{eff}$ may be given by the equation:

$$C_{eff} = Q_0^{1/\alpha} \times \left(\frac{1}{R_1} + \frac{1}{R_2}\right)^{(\alpha-1)/\alpha}$$

In a variant, the effective capacitance $C_{eff}$ may be given by the equation $$C_{eff} = Q_0^{1/\alpha} \times R_1^{(1-\alpha)/\alpha}$$

Preferably, the effective capacitance is determined based at least on a surface distributed model of the first constant phase element. In a variant, or additionally, the effective capacitance is determined based at least on a thickness distributed model of the first constant phase element.

The method may comprise delivering based at least on the comparison at least one information relating to:
- a composition of the cellular structure;
- a number of layers of cells present in the cellular structure.

In some embodiments, there is provided a method for monitoring healing following implant of a surgical device, comprising performing the method as defined above for determining at least one type and/or condition of cells of a cellular structure in vicinity to the surgical device, and representative of an evolution of the healing process.

The surgical device may be one of a stent, scaffold, graft, catheter, guidewire, probe, occlude device, heart valve, pacemaker, ICD. The device may be permanently implanted or not. The device may be implanted and withdrawn.

In some embodiments, there is provided a method for evaluating a response of a cellular structure to at least one stimulus, comprising performing the method as defined above to determine at least one type and/or condition of cells of the cellular structure representative of the response to the at least one stimulus.

The stimulus may be a chemical, bio-chemical or biological stimulus.

Exemplary embodiments also relate to a system, notably for performing a method as defined above, comprising:
- A measuring unit comprising at least a couple of electrodes for measuring an impedance spectrum of a cellular structure,
- a computing unit configured for computing at least one value representative of an effective capacitance $C_{eff}$ of the cellular structure, the effective capacitance $C_{eff}$ being based on at least one equivalent circuit model of the impedance of the cellular structure including at least a first constant phase element having a pseudo-capacitance, the effective capacitance $C_{eff}$ being dependant at least on the pseudo-capacitance of the first constant phase element and on at least one electrical resistivity quantity of said equivalent circuit model.

The computing unit may be further configured for comparing at least one value representative of the effective capacitance $C_{eff}$ of the cellular structure to at least one reference value determined for at least one known type and/or condition of cells and determining based at least on this comparison at least one type and/or condition of cells of the cellular structure.

The system may be an implantable surgical device.

The system may comprise an implantable surgical device comprising the measuring unit and a wireless transmitter, the computing unit being external to the implantable surgical device and comprising a receiver for receiving data transmitted by said wireless transmitter. The implantable surgical device may be one of a stent, scaffold, graft, catheter, guidewire, probe, occlude device, heart valve, pacemaker, ICD a stent.

In some embodiments, there is provided a method for discriminating cells of a cellular structure, notably of a cellular tissue, comprising:
a) determining a frequency spectrum of the impedance of the cellular structure;
b) defining at least one model of the impedance of the cellular structure including a constant phase element;
c) determining the impedance of the constant phase element which optimizes the correlation of each model of the impedance of the cellular structure with the spectrum determined in a);
d) deducing, from the impedance of the constant phase element or from the impedances of the constant phase elements determined in c), an item of information on the cells of the cellular structure.

The use of a model with a constant phase element may make it possible to deduce more accurate information on the cellular structure tested.

According to some embodiments, the method may present one or more of the following features, taken alone or in combination:
step d) consists of two sub-steps:
d1) deducing, from the impedance of each constant phase element and, optionally, from the parameters which optimize the correlation of each model of the impedance of the cellular structure with the spectrum determined in step a), an effective capacitance representative of a set of individual capacitances of elements of the cellular structure; and
d2) deducing, from the effective capacitance or from the effective capacitances determined in step d1), an item of information on the cells of the cellular structure;
in step d1), the effective capacitance is determined by identifying the impedance of the cellular structure and the impedance of an electrical model grouping together individual circuits in parallel, each individual circuit comprising at least one individual resistance and at least one individual capacitance, the effective capacitance being representative of the capacitance resulting from all the individual capacitances;
each individual circuit comprises, preferably consists of, a first individual resistance in series with a parallel mounting of an individual capacitance with a second individual resistance, the effective capacitance being equal to the sum of the individual capacitances;
in step d1), the effective capacitance is determined by identifying the impedance of the cellular structure and the impedance of an electrical model comprising a first resistance mounted in series with a parallel mounting of a second resistance with the effective capacitance;
in step a), a frequency spectrum of the real part and/or of the imaginary part and/or of the modulus and/or of the phase of the impedance of the cellular structure is determined;
step d) comprises a sub-step of comparison of the parameters of the impedance of the constant phase element and/or of the model of the impedance of the cellular structure and/or of the effective capacitance of the cellular structure with pre-established values, corresponding notably to tests performed on one or more cellular structures of known compositions;
in step d), the item of information on the cells of the cellular structure comprises at least one out of:
the type of cells of the cellular structure;
the composition of the cellular structure;
the number of layers of cells present in the cellular structure; and
the condition of the cells, notably the inflamed condition, the cancerous condition, the healthy condition of the cells, or the undifferentiated or differentiated condition of stem cells;
the item of information being deduced, if appropriate, from the comparison of the parameters of the model of the impedance of the cellular structure and/or from the determined effective capacitance, with one or more pre-established values;
step a) consists in:

i) establishing contact between the cellular structure and at least two electrodes, preferably four electrodes;
ii) applying an alternating current between the implanted electrodes;
iii) varying the frequency of the alternating current and determining the corresponding current voltage and intensity;
iv) calculating the impedance by determining the ratio between the voltage and the intensity;

a model of the impedance of the cellular structure comprises, preferably consists of, a first resistance mounted in series with a parallel connection of the constant phase element and of a second resistance, the model further including, preferably, a second constant phase element, mounted in series with the first resistance;

said one model of the impedance of the cellular structure further includes a third resistance, mounted in parallel with the series connection of the first resistance with the second resistance and the constant phase element in parallel and, preferably, the second constant phase element, if appropriate;

a model of the impedance of the cellular structure comprises, preferably consists of, the parallel connection of a resistance, on the one hand, and of a resistance mounted in series with the constant phase element, on the other hand;

the impedance $Z_{CPE}$ of the constant phase element is of the form:

$$Z_{CPEm} = \frac{1}{(j\omega)^\alpha Q_0},$$

in which:
j is the square root of −1;
ω is the pulsing of the current passing through the impedance;
$Q_0$ is a real number (pseudo-capacitance); and
α is a real number lying between 0 and 1,
the parameters $Q_0$ and a being determined in the step c);

in step d1), the effective capacitance is given by the equation:

$$C_{eff} = Q_0^{1/\alpha} \times \left(\frac{1}{R_1} + \frac{1}{R_2}\right)^{(\alpha-1)/\alpha}$$

in which R1, R2 and $$Z_{CPE} = \frac{1}{(j\omega)^\alpha Q_0}$$

are the respective impedances of a first resistance mounted in series with a second resistance in parallel with a constant phase element to form a computation model, these impedances being determined to correlate the model of the cellular structure with the computation model, as a function of the parameters of the model of the cellular structure;

in step b), a single model of the impedance of the cellular structure is chosen and, in step c), a single form of the impedance of the constant phase element is chosen; and in step b), a number of models of the impedance of the cellular structure are chosen, and/or, in step c), a number of forms of the impedance of the constant phase element are chosen, a choice of the model of the impedance of the cellular structure and/or of the form of the impedance of the constant phase element being made during a step A), between step c) and step d), which optimizes/optimize a criterion of correlation of the model of the impedance with the cellular structure, the criterion of correlation being, for example, the minimization of the standard deviation between the model of the impedance of the cellular structure and the spectrum determined in step a).

In some embodiments, there is provided a system for implementing a method as described hereinabove in all its combinations, comprising:
means for measuring an impedance of a cellular structure; and
an electronic control unit linked to the measurement means, for implementing the method as defined above.

According to some embodiments, the system presents one or more of the following features, taken alone or in combination:
the measurement means comprise an alternating current generator, linked to two, preferably four, electrodes intended to be in contact with the cellular structure, and a device for measuring the voltage or the intensity of the current between two of said electrodes, the corresponding impedance then being able to be determined in said electronic control unit; and
said measurement means comprise a medical device, notably a medical device that may be implanted in the human body or may be applied to the human body, to which the electrodes are fixed, the medical device then preferably being adapted to communicate, without contact with the outside of the body of a patient, an item of information relating to the impedance or to the intensity and to the voltage of the current between the electrodes.

Other features and advantages of various embodiments will become apparent on reading the following detailed description, said description referring to the attached drawings in which.

Figure 16:
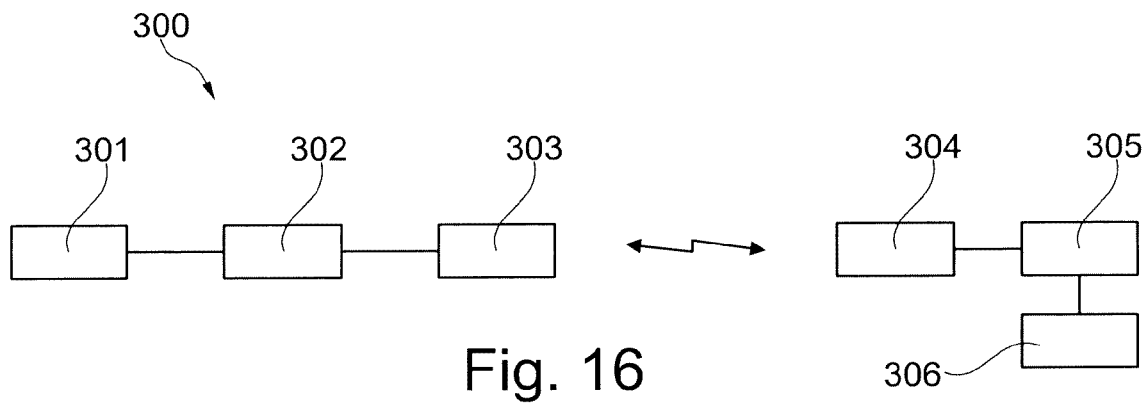
Figure 17:
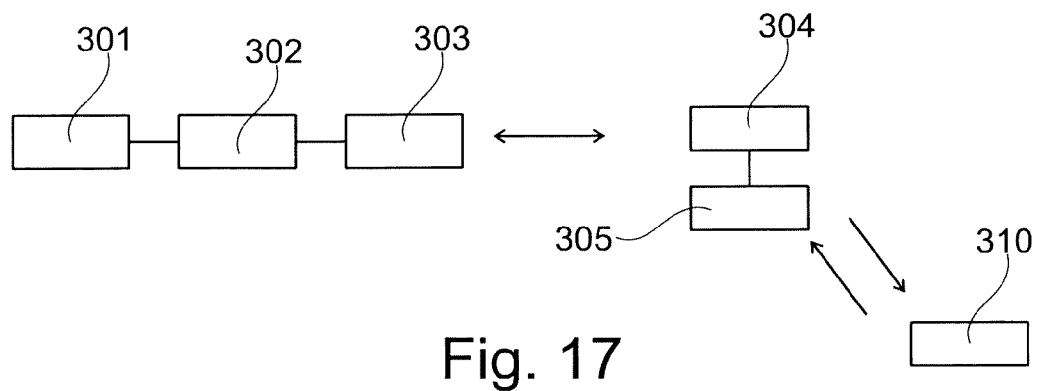
Figure 12A:
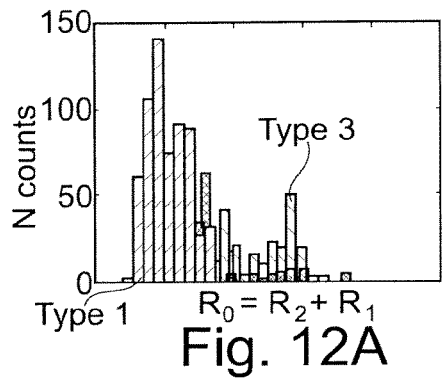
Figure 12B:
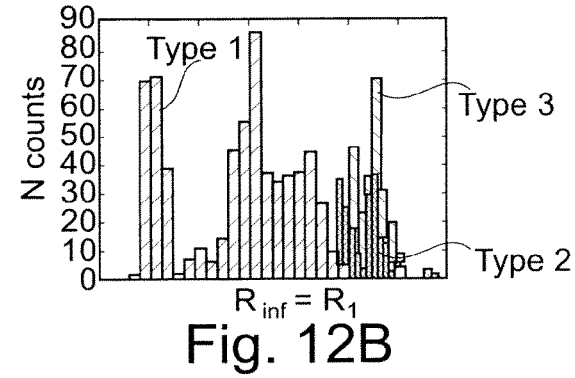
Figure 12C:
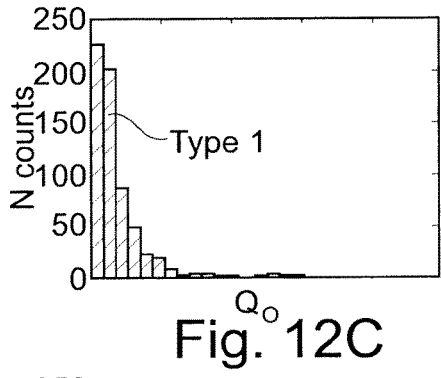
Figure 12D:
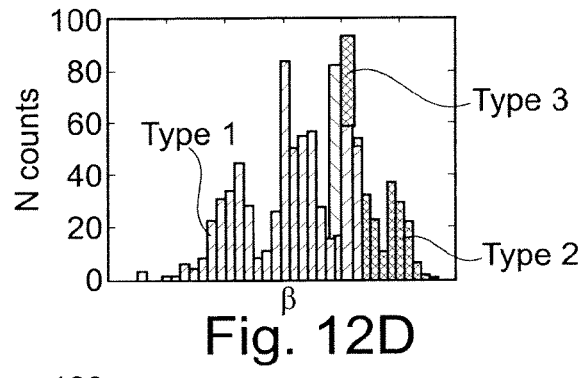
Figure 12E:
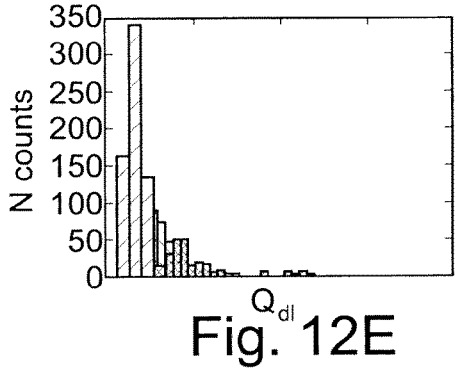
Figure 12F:
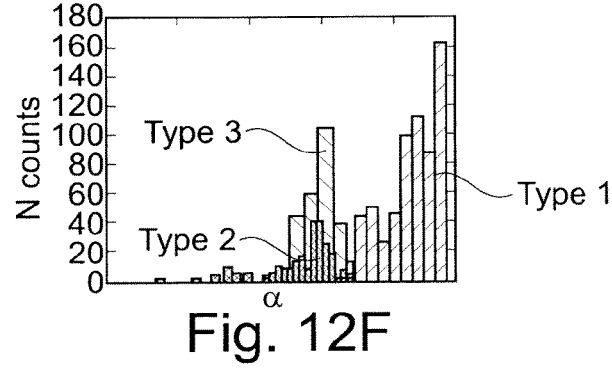
Figure 13:
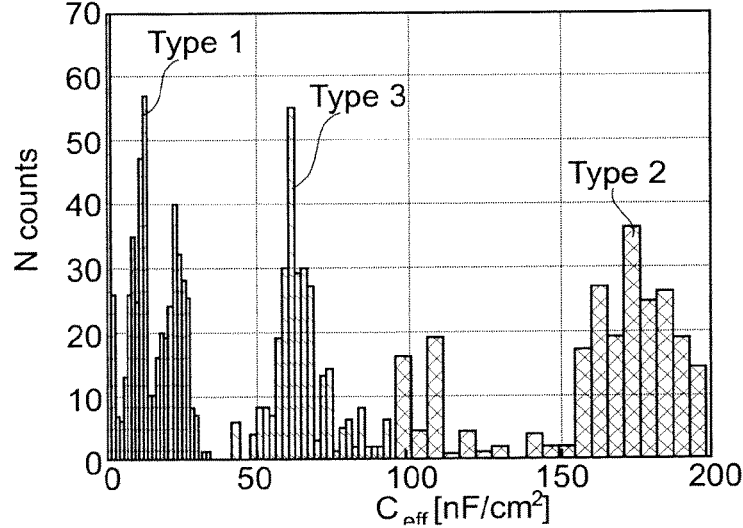
Figure 14:
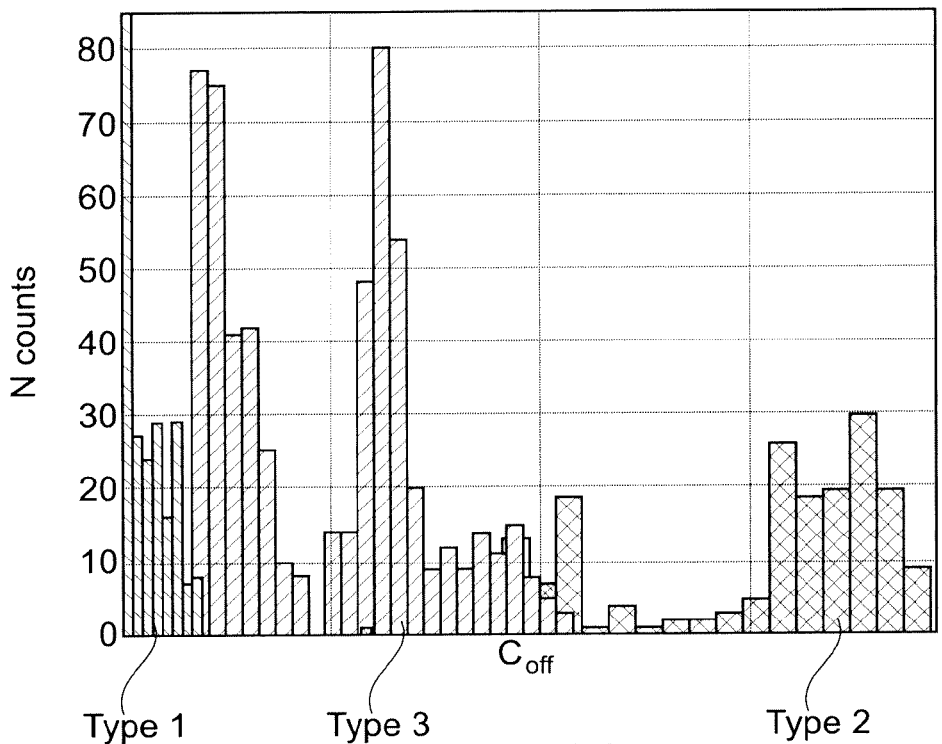
Figure 15:
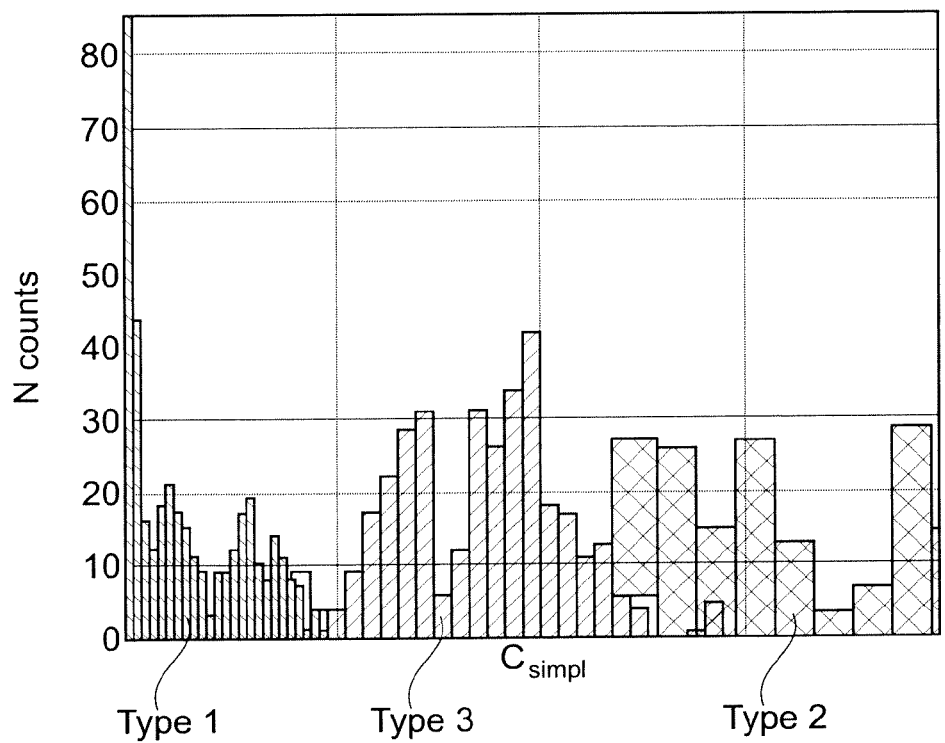

FIGS. 11A and 11B, and 12A to 12F show various parameters distributions;

FIGS. 13 to 15 show distributions of values representative of effective capacitance for different cell types;

FIGS. 16 and 17 show examples of systems made in accordance with the present invention.

In some embodiments, a method allows for a discrimination of cells of a cellular structure, notably of a cell tissue. "Discrimination" should be understood here to include the possibility, given by this method, of distinguishing cells, for example of determining the type of cells of the tissue. More generally, the discrimination made possible by the method consists in determining at least one item of information relating to cells in a tested tissue. Examples of information items that may be determined by virtue of this method are given later.

Figure 1:
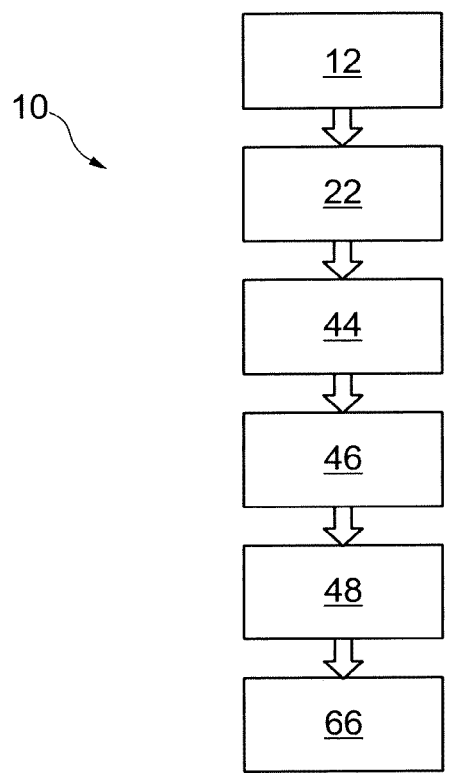
FIG. 1 is a flow diagram of an exemplary method for discriminating cells in a tissue.
Figure 2:
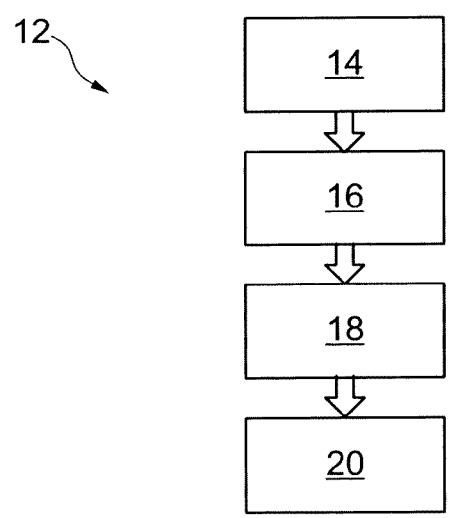
FIG. 2 is a flow diagram of an exemplary method for determining, from a frequency spectrum, the impedance of a tissue.

The cell discrimination method 10, as illustrated schematically in FIG. 1, comprises a first step 12 of determining a frequency spectrum of the impedance of a cellular structure to be tested. Hereinbelow, the structure of a tissue of cells will be taken as example of cellular structure.

Spectrum should be understood here to include a set of pairs of values of the impedance of the tissue, the latter being able to be complex, and of the corresponding frequency. This spectrum may thus be discrete and comprise only a finite number of pairs. These pairs may notably be separated by several Hz, even by several tens of Hz, even by several hundreds of Hz. However, preferably, the spectrum determined in this step is continuous, pseudo-continuous or discretized, over a frequency band. Pseudo-continuous should be understood to mean that the spectrum is determined for successive frequencies separated by 100 Hz or less, preferably by 10 Hz or less, preferably even by 1 Hz or less. The frequency band over which the impedance of the tissue is determined extends, for example, from 10 kHz, preferably 100 kHz. In effect, at low frequencies, the membrane of the cells of the tissue acts as an electrical insulator, so that the impedance is very high and, above all, varies little. Moreover, the frequency band over which the impedance of the tissue is determined extends, for example, up to 100 MHz, preferably 1 MHz. In effect, at high frequencies, the wall of the cells that makes up the tissues become transparent from an electrical point of view. The measured impedance is therefore no longer representative of the cell wall. This spectrum may be a frequency spectrum of the real part and/or of the imaginary part and/or of the modulus and/or of the phase of the complex impedance of the cellular structure.

This first step 12 of determination of a frequency spectrum of the impedance of the tissue may notably be performed as described hereinbelow.

First of all, during a step 14, two, preferably three, even more preferably four electrodes are placed in contact with the tissue to be tested, the electrodes being linked to an alternating current generator. The measurement with four electrodes is preferred because it makes it possible to implement two electrodes to pass the current into the tissue to be tested and to measure the potential difference between the other two electrodes. This makes it possible to improve the accuracy of the measurement. Then, during a step 16, an alternating current is applied between the electrodes implanted in the tissue. Then, by varying the frequency of the current applied during a step 18, the corresponding voltage is measured, at the terminals of the electrodes for different frequencies. Finally, during a step 20, the ratio between the voltage measured and the current applied is calculated, for each of the frequencies for which the measurement has been performed. This ratio gives the impedance of the tissue tested, as a function of the measurement frequency. The calculated ratios make it possible to define a frequency spectrum of the impedance of the tissue.

Figure 3:
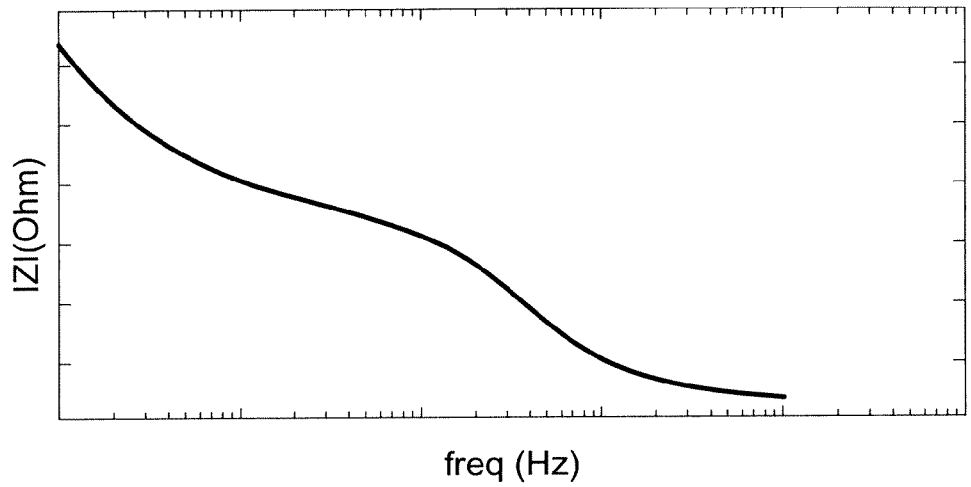
FIG. 3 represents an exemplary frequency spectrum of the modulus of the impedance of a cell tissue.

When the spectrum is continuous or pseudo-continuous, it may be represented as illustrated in FIG. 3, in the form of a curve giving, in this particular case, the modulus of the impedance of the tissue as a function of the frequency, the latter being plotted according to a logarithm scale. It should be noted here that a logarithmic scale is used on the x axis.

In a step 22 of the discrimination method 10, different models of the impedance of the tissue, that is to say different electrical circuits that may model the tissue, are then chosen. Here, models are chosen that include a constant phase element, and not a capacitance. In effect, it has been found that a constant phase element models more realistically the behaviour of the tissue than a capacitance.

A constant phase element (or CPE) has an impedance $Z_{CPE}$ of the form:

$$Z_{CPE} = \frac{1}{(j\omega)^\alpha Q_0} \quad [1]$$

in which:
j is the square root of −1 ($j^2=-1$);
ω is the specific pulsing of the current (ω=2πf, in which f is the frequency of the current);
$Q_0$ is a real parameter of the constant phase element, also referred to as pseudo-capacitance; and
α is another real parameter of the constant phase element, lying between 0 and 1, such that the phase $\varphi_{CPE}$ of the constant phase element is equal to −απ/2.

Hereinafter in the description, a constant phase element whose impedance is given by the equation [1] above is chosen by way of example.

The models of the impedance of the tissue may notably be chosen from those described hereinbelow, with respect to FIGS. 4 to 7. Obviously, the simpler the model, the simpler the calculations. However, a complex model may better correlate to the spectrum of the impedance obtained by the measurement and therefore give more accurate results.

Figure 4:
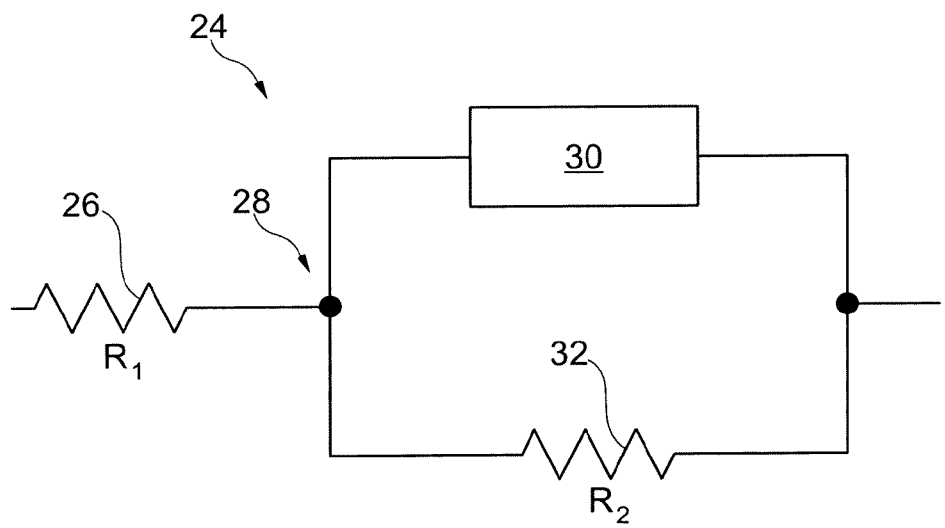
FIGS. 4 to 7 illustrate exemplary models of the impedance of the tissue, that may be implemented in the method of FIG. 1, including a constant phase element.

According to a first model 24 illustrated in FIG. 4, the impedance of the cell tissue is modelled by a first resistance 26 mounted in series with a parallel connection 28 of a constant phase element 30 and of a second resistance 32.

In this case, the total resistance $Z_{tot}$ of the cell tissue is of the form:

$$Z_{tot} = R_1 + \frac{R_2}{1 + (j\omega)^\alpha Q_0 R_2}, \quad [3]$$

in which:
$Z_{tot}$ is the total impedance of the first model 24 representing the cell tissue;
R1 and R2 are the resistance values of the first 26 and second 32 resistances.

Such a model describes particularly well a tissue covering measurement electrodes, like a set of individual parallel mountings, each individual mounting being made up of an individual resistance in series with a parallel mounting of an individual resistance and of an individual capacitance. Such a mounting may make it possible to model a distribution of the time constant over all of the surface of the measurement electrodes, according to different circuits in parallel whose parameters may be different, each of these circuits in parallel representing a cell of the tissue. Thus, the fact that the cells of the tissue may exhibit different electrical properties, notably a different resistance and/or capacitance, may be modelled.

Figure 5:
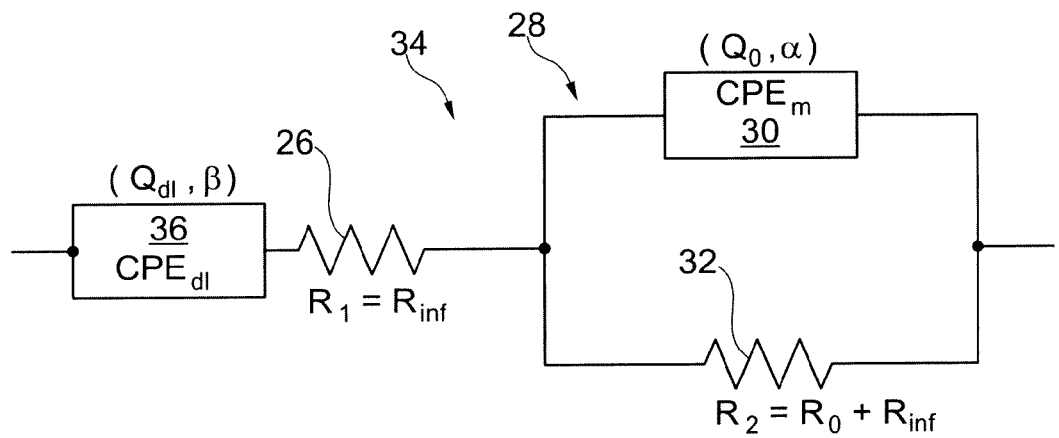

A second model 34, illustrated in FIG. 5, complements the model 24 of FIG. 4, by the series mounting of a second constant phase element 36. The impedance $Z_{CPE,2}$ of this second constant phase element 36 may also be chosen to be of the form:

$$Z_{CPE,2} = \frac{1}{(j\omega)^\beta Q_1}, \quad [4]$$

in which:
- $\beta$ is a real parameter lying between 0 and 1, such that the constant phase of this second constant phase element is equal to $-\beta\pi/2$; and
- $Q_1$ is a pseudo-capacitante (real number) of the constant phase element, also referred to as $Q_{d1}$ for double layer pseudo-capacitance.

The total impedance $Z_{tot}$ of the tissue according to this second model 34 is therefore given by the following equation:

$$Z_{tot} = \frac{1}{(j\omega)^\beta Q_1} + R_1 + \frac{R_2}{1 + (j\omega Q_0)^\alpha R_2}. \quad [5]$$

Figure 5A:
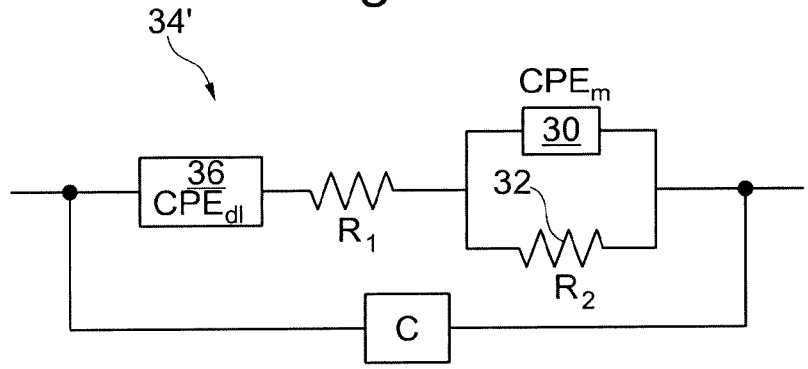

A variant 34' of the second model 34 is shown in FIG. 5A, and differs from the model of FIG. 5 by the addition of a capacitance C in parallel with the circuit of FIG. 5, for a better fit of the impedance curve at high frequencies.

Figure 6:
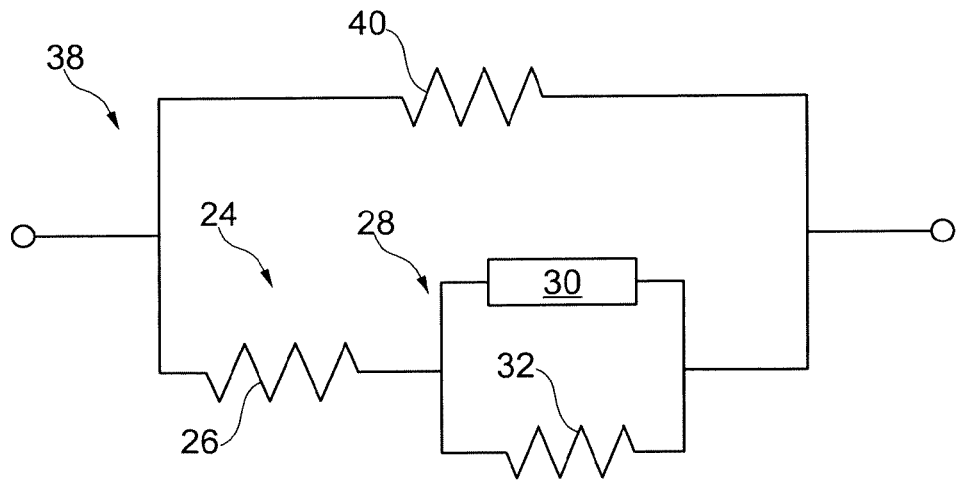

A third model 38, illustrated in FIG. 6, corresponds to the model of FIG. 4, mounted in parallel with a third resistance 40, of resistance $R_3$. In this case, the total impedance $Z_{tot}$ of the tissue is given by the equation:

$$\frac{1}{Z_{tot}} = \frac{1}{R_3} + \frac{1}{R_1 + \frac{R_2}{1 + (j\omega Q_0)^\alpha R_2}}. \quad [6]$$

Figure 7:
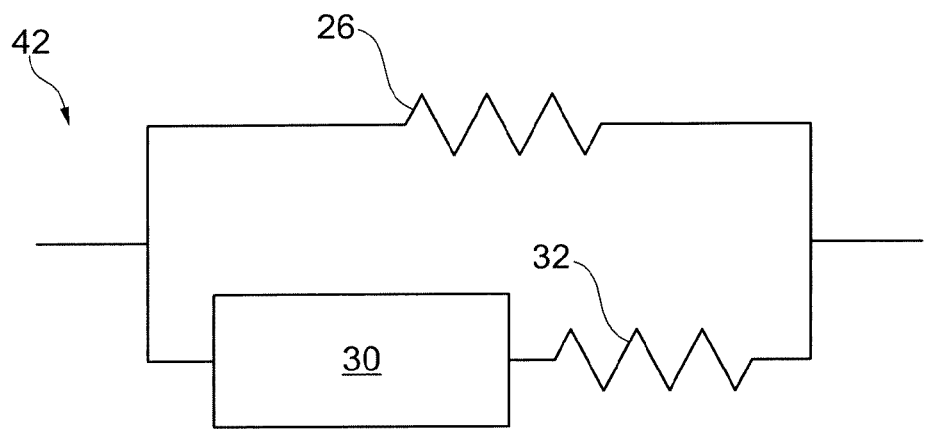

Finally, a fourth exemplary model 42 is illustrated in FIG. 7. This model 42 comprises, as illustrated, a first resistance 26, mounted in parallel with a series mounting of a constant phase element 30 and of a second resistance 32.

The total impedance $Z_{tot}$ of the tissue is given, for this model 42, by the equation:

$$\frac{1}{Z_{tot}} = \frac{1}{R_1} + \frac{R_2}{1 + (j\omega Q_0)^\alpha R_2} \quad [7]$$

The discrimination method then continues with a step 44, during which, for each model chosen in step 22, the impedance of the constant phase element 30 and all other components of the model are determined so that the impedance of the model matches to some extent the spectrum determined in step 12.

This step of improving the matching of the model of the impedance of the tissue with the spectrum determined in the step 12 may be implemented by any optimization method known by those skilled in the art. By way of example, the least squares method may be implemented, which allows for a practical and relatively simple implementation of this step 44.

An intermediate step 46 of the discrimination method 10 may then be provided. This step 46 consists in determining the model which seems to improve the matching between the model and the measured impedance. This model may for example be that which minimizes the standard deviation with the measured spectrum. Hereinafter in the description, the case in which the model 24 is retained as that correlating best to the measured spectrum of the impedance of the tissue is assumed.

During a step 48, an effective capacitance of the cell tissue is deduced from the parameters of the impedance of the constant phase element and from the corresponding model.

Theoretically, this effective capacitance is representative of a set of individual capacitances of elements of the cell structure. The effective capacitance is representative of distributed local capacitances of elements of the cell structure. These elements of the cell structure may notably be all or some of the nuclei of the cells of the cellular structure and also other parts of the cells such as the golgi apparatus, vesicles, mitochondrion, lysosome and other elements which may play a role in membrane interaction. The effective capacitance may also be influenced by the geometry of cells and the space between cells. The effective capacitance is a model which allows for a representation of the electrical membrane behaviour of a part or of all of a cellular structure. This model makes it possible to relevantly discriminate the cells. It differs from the membrane capacitance at least for the reason that it does not take for value the resultant capacitance of the electrical measurement but rather is given by a distributed model that is equivalent to a distribution of local capacitances.

More practically, this effective capacitance is determined by identifying the impedance of the chosen cellular structure with a model comprising individual parallel mountings, each individual mounting comprising at least one individual resistance and one individual capacitance. Each mounting may notably comprise, preferably consist of, a first individual resistance in series with a parallel mounting of an individual capacitance with a second individual resistance. These individual mountings aim to model the behaviour of each cell of the cellular structure.

In the case of the model 24 (or 34 or 34'), the determination of the effective capacitance may notably be performed as follows. The impedance of the model 24 with a constant phase element is compared with the impedance of an equivalent or identical model, in which the constant phase element is replaced by an effective capacitance. The calculation, strictly speaking, of the effective capacitance may then be performed by comparing the real part and/or the imaginary part and/or the phase and/or the modulus of the impedance of the model chosen for the cellular structure with a constant phase element with the identical model in which the constant phase element is replaced by an effective capacitance.

In the case of the model 24 (or 34 or 34'), for example, by introducing a time constant $$\tau_0 = C_{eff} \frac{R_1 R_2}{R_1 + R_2}$$

into the equation of the admittance of the model 24, directly deduced from the equation [3], the equation [8] below is obtained:

$$Y_{tot} = \frac{1}{R_1}\left[1 - \frac{R_2}{R_1+R_2}\left(1 + \frac{R_1 R_2}{R_1+R_2}Q_0(j\omega)^\alpha\right)^{-1}\right] = \quad [8]$$
$$\frac{1}{R_1}\left[1 - \frac{R_2}{R_1+R_2}(1+(j\omega\tau_0)^\alpha)^{-1}\right],$$

from which a formula for the effective capacitance may be deduced, in the form:

$$C_{eff} = Q_0^{1/\alpha} \times \left(\frac{1}{R_1} + \frac{1}{R_2}\right)^{(\alpha-1)/\alpha} \quad [9]$$

In the case where another model of impedance of the cellular structure with a constant phase element is chosen, it is possible to determine a corresponding equation of the effective capacitance. To do this, it is sufficient to calculate the impedances $R_1$, $R_2$, $Z_{CPE}$ and $Z_{CPE,2}$, if appropriate, of the model 24 or 34 or 34', as a function of the parameters of the chosen model, for the model 24 or 34 or 34' to be electrically equivalent to the model of the impedance of the chosen cellular structure. The effective capacitance may then be calculated by replacing $R_1$, $R_2$, $Z_O$ and $\alpha$ with the corresponding values, expressed as a function of the parameters of the chosen model.

The cell discrimination method 10 then continues with a step 66 of deduction of an item of information on the cells of the tissue, from the effective capacitance determined previously.

This deduction may be made by comparing the value of the effective capacitance determined in the step 48 with pre-established effective capacitance values. The pre-established effective capacitance values may have been obtained during tests performed on tissues of known compositions (e.g., types of cells and/or conditions of cells), in known media, and with known test conditions. The pre-established values may be grouped together in a database (or other form of data structure or data storage) of effective capacitance values, grouping together the effective capacitances measured for different types of cells and/or different conditions of different cells and/or in different test conditions. The effective capacitance value may be compared to a database of effective capacitances of cell type and condition susceptible to be found in the present measurement.

For the comparison, the effective capacitance Ceff may be used together with other parameters. The comparison may not be an exact match and includes the determination whether the effective capacitance value falls or not within a pre-determined range.

It is thus possible to discriminate the cells of the tissue, that is to say to determine at least one of the following items of information:
the type of cells in the tissue;
the composition of the tissue, notably if the latter is composed of different types of cells or of cells in different conditions;
the number of layers of cells present in the tissue; and/or
the condition of the cells, notably if the cells are in a healthy condition, in an inflamed condition, in a degenerated condition, notably if there are one or more cancerous cells, in an infected condition or if they are differentiated.

Figure 8:
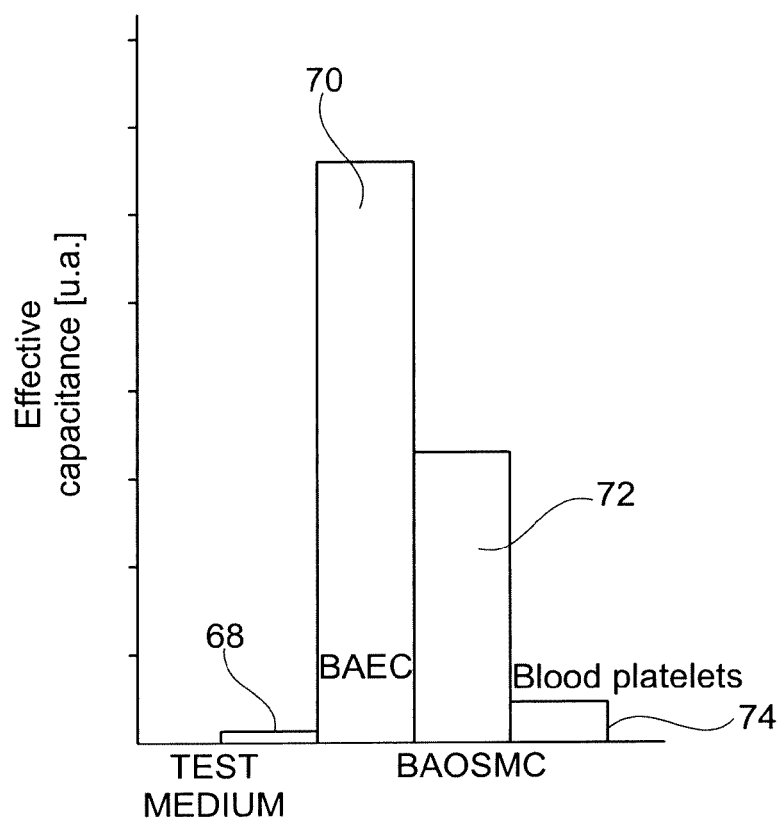
FIG. 8 shows an example, in diagram form, of effective capacitances of cellular structures determined by means of the method of FIG. 1.

As an example, FIG. 8 represents, in diagram form, the effective capacitances 68, 70, 72, 74 determined in the context of a test conducted according to the method described previously.

In the context of a test, cells were cultivated until the confluence of the cells was obtained. In the case of the exemplary test which was conducted, two days of culture were required in an incubator at 37° C. and 5% $CO_2$, to obtain, by confluence, the tissues to be tested. The determination of the spectrum of the impedance of the different tissues to be tested was performed using an impedance spectroscopy system. The spectrum was determined between 1 kHz and 10 MHz, by applying an alternating voltage estimated to be fairly low so as not to electrically excite the cells being studied, but sufficient to have correct measurements. In the example of the test conducted, an amplitude of 20 mV of the alternating voltage was retained.

The effective capacitance 68 is that of the test medium, static, alone. This test medium is a cell culture medium. The effective capacitance 70 is that of bovine aortic endothelial cells (BAEC). The effective capacitance 72 is that of bovine aortic smooth muscle cells (BAOSMC). Finally, the effective capacitance 74 is that of blood platelets (or thrombocytes). As this diagram shows, the effective capacitances of the different types of cells exhibit values clearly different from one another, which makes it possible to effectively distinguish between the different types of cells with accuracy, without risk of confusion.

Thus, one advantage of the discrimination method of some embodiments described above is that it allows for the discrimination of cells in a cellular structure, notably in a confluent and single-layer cellular structure, covering the electrodes, from a simple measurement of a frequency spectrum of an impedance of the structure to be tested. The results obtained are accurate. There is no need to proceed with a normalization of the measured impedance, nor to proceed with a reference measurement in the absence of any sample to be tested. The method may thus be implemented in vivo, that is to say without the need for prior sampling of cells or of a cellular structure to be tested.

It should be noted, in the case where an effective capacitance is determined, a single value for effective capacitance, at one time, may be sufficient to discriminate the cells of the tissue. This is in contrast with other techniques performing an analysis of a capacitance that require multiple determinations of capacitance over time. In these embodiments, the parameters of the chosen model of the impedance of the cellular structure to be tested may also be compared to pre-established values to specify the result of the comparison of the effective capacitance. For example, when the cells are inflamed, the junction between the cells is looser. The resistance at low frequency—that is to say the resistance 32 of the model 24 for example—is then lower, compared to healthy cells. A comparison of the value of this resistance with a value pre-established for healthy, non-inflamed cells may then make it possible to determine the inflamed condition of these cells.

It should also be noted that other parameters of a model of impedance, aside from effective capacitance, may be considered to discriminate the cells. In some embodiments, these other parameters may also make it possible to determine additional items of information on the cellular structure tested. Thus, for example, $R_2$ or the sum $R_1+R_2$ of the resistances 26, 32 of the model 24 may be considered to determine the thickness of the cellular structure. To do this, in some embodiments the values $R_2$, and possibly $R_1$, are determined, notably concomitantly with the determination of the impedance of the constant phase element, so as to optimize the correlation of the model 24 with the measured impedance spectrum. The value $R_2$ or the sum $R_1+R_2$ may then be compared to corresponding values, predetermined in known conditions, for example in vitro. These predetermined values may notably be stored in database (or another data structure) form.

As conditioned previously, the method may easily be implemented in the context of devices that may be implanted in the human body or applied to the human body.

Figure 9:
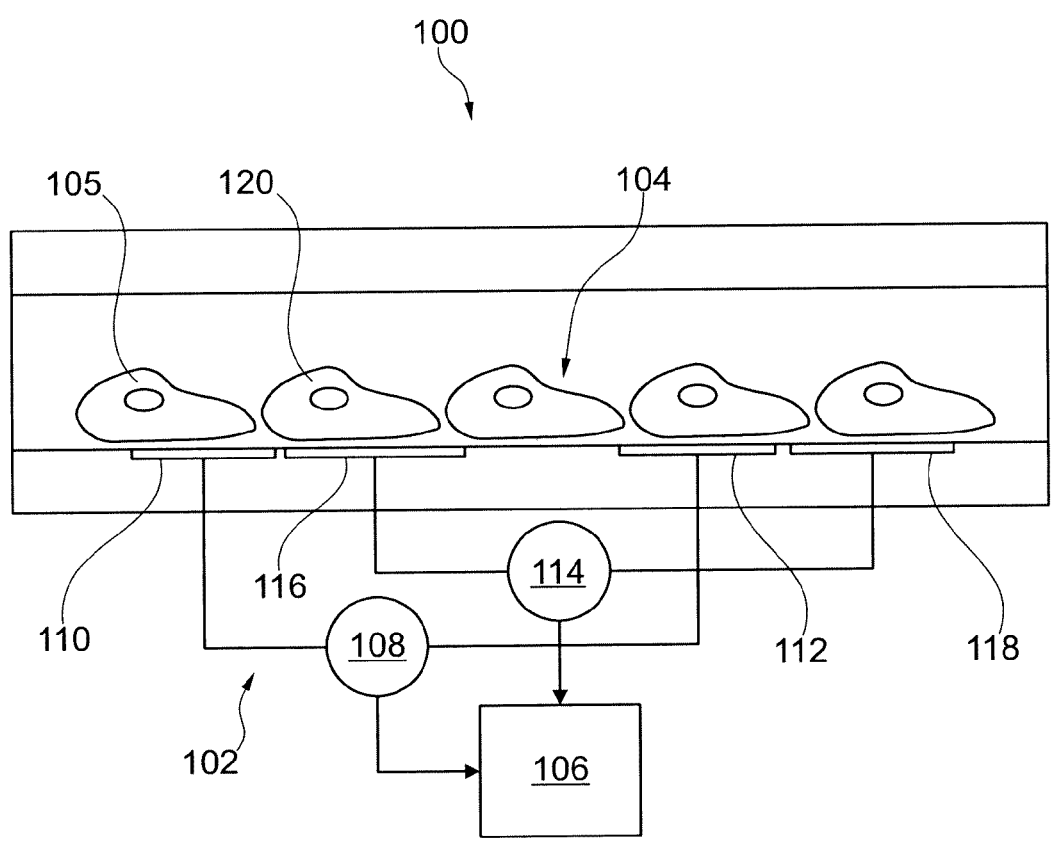
FIG. 9 illustrates an exemplary system for implementing the method of FIG. 1.

By way of example, FIG. 9 illustrates an example 100 of a system for implementing a method of some embodiments as described previously.

The system 100 essentially comprises means 102 for measuring the impedance of a cellular structure 104, here a single-layer tissue of confluent cells, dipped in a medium 105, for example blood, and an electronic control unit 106, linked to the measurement means 102, to implement the method and discriminate the cells of the cellular structure 104 as a function of the measured impedance.

The measurement means 102 here comprise an electrical generator 108 of alternating current, linked to two electrodes 110, 112 in contact with the cellular structure 104. The measurement means 102 also comprise a device 114 for determining the intensity passing through the cellular structure 104, linked to said cellular structure 104 by two electrodes 116, 118 in contact with the cellular structure 104. The electronic control unit 106 is linked to the electrical generator 108 and to the intensity measurement device 114, in order to be able to determine the impedance of the cellular structure 104, for example from the measurement of the voltage and of the intensity at the terminals of the electrodes 110, 112, 116, 118.

The electrodes 110, 112, 116, 118 consist of an electrically conductive material, such as gold for example.

Here, advantageously, the measurement means 102 further comprise a medical device 120 that may be implanted in the human body, here a stent 120, or that may be applied to the human body. In this case, the electrodes 110, 112, 116, 118, the alternating voltage generator and the intensity measurement device may be fixed onto this medical device. The medical device is for example as described in the application FR3026631 A1 MEDICAL DEVICE PROVIDED WITH SENSORS HAVING VARIABLE IMPEDANCE filed on 2014 Oct. 3, the entire contents of which, and in particular the discussion of implantable medical devices including measurement devices, are incorporated herein by reference.

In this case, the alternating electrical generator 108 may include an armature, such as the body of the medical device or an antenna electrically insulated from the body of the medical device, adapted to emit an electrical current under the effect of an electromagnetic field emitted by an interrogation unit external to the stent 120. The electrodes may then form a sensor with variable impedance, the impedance of which varies as a function of the cellular structure which covers them. Finally, the electronic control unit may receive an item of information relating to the impedance between the electrodes, notably by emission of a magnetic field by an antenna fixed onto the body of the implantable medical device 120.

The stent 120 may thus make it possible to check the correct progress of the healing of the endothelium, after the stent 120 has been fitted. In effect, such a stent 120, in cooperation with the electronic control unit, makes it possible to determine, by implementing the method of FIG. 1, whether the cellular structure which is formed on the surface of the endothelium essentially comprises healthy endothelial cells, inflamed endothelial cells, smooth muscle cells and/or platelets.

The invention is not limited to the examples described hereinabove and numerous variants are possible, while within the scope of the definition given by the attached claims.

Thus, for example, it is possible to choose a single model of the impedance of the tissue in the step 22. In this case, it is not necessary to carry out the optimization for a number of models. The method is therefore simpler and faster to implement in this case. It is notably possible to proceed in this way when a model is considered as more relevant.

Moreover, in the examples described, the discrimination of the cells is based essentially on the calculated effective capacitance and on its comparison with pre-established values. As a variant, however, it is possible to proceed with the discrimination of the cells from parameters of the chosen model of the impedance of the cellular structure. However, it seems that the comparison of just the value of the effective capacitance is both simple and allows for a reliable discrimination of the cells.

FIG. 16 shows an example of a system 300 made in accordance with the present invention. This system comprises a measurement module 301 with may be part of an implanted device, for example a stent, or of a device for in vitro cultivation of cells.

The measurement module comprises at least two electrodes and may be as described above with reference to FIG. 9.

The system 300 also comprises an internal processing unit 302 that is configured for example to generate an impedance spectrum from data from the measurement module.

The system 300 may comprise an emitter 303 to wirelessly transmit data (the data from the measurement module 301 and/or the impedance spectrum determined by the internal processing unit 302) to a receiver 304, which may be external to the body in case the measurements take place in vivo. The transmission may take place under any wireless protocol such as RFID, NFC, Bluetooth, Wifi, either radio or Infrared, inter alia. In some embodiments, the transmission may include transmission via one or more wired and/or wireless local and/or wide-area networks, including the Internet.

The system 300 may comprise an external processing unit 305 to compute the impedance spectrum (in the case of receiving from the emitter 303 the data from the measurement module 301) and/or the various parameters and effective capacitance $C_{eff}$ based on the received data and display means 306 such as a LCD screen to display information relating to the type and/or condition of cells determined based upon comparison of a value representative of $C_{eff}$ with reference data. To determine the various parameters and effective capacitance, the external processing unit 305 may be configured with information regarding one or more equivalent circuit models for an impedance, and determine the parameters of at least one of the model(s), such as in the manner discussed above. The external processing unit 305 may also be configured to select one of the models, following determination of the parameters of the model(s), as a model from which to determine the effective capacitance, as discussed above. The external processing unit may make the selection based on a degree of fit between the equivalent circuit model and the impedance spectrum. The system may provide, based on the at least one type and/or condition of cells thus identified, information representative of an evolution of a healing process, for example, information regarding a current status of an area in which (e.g., tissue to which) a procedure was performed (including positioning of an implant such as a stent) and/or provide information regarding a change over time in the status of the area that may be reflective of a response to the procedure in the area, such as a healing or scarring response.

The external processing unit may be a special-purpose device that includes specialized hardware such as an ASIC, EEPROM, or other component specially configured to perform the operations of the external processing unit described above. In other embodiments, the external processing unit may be a general-purpose device such as a laptop or desktop personal computer, a server, a smart/mobile phone, a personal digital assistant, a tablet computer, or other computing device including mobile computing devices. In the case that the external processing unit is implemented with a general-purpose device, the general-purpose device may include one or more processors and a non-transitory computer-readable storage medium (e.g., an instruction register, an on-chip cache, a memory, a hard drive, a removable medium such as an optical medium) having encoded thereon instructions for execution by the processor(s), where the instructions cause the processor to carry out the operations described above as performed by the external processing unit. The internal processing unit may, in some embodiments, be any appropriate IC chip or other hardware component with processing capabilities. The external and internal processing units may be located proximate to one another (e.g., within a same room, or within 5 feet) or may be located remote (e.g., in different parts of a building or complex of buildings) or geographically remote (e.g., miles apart) from one another, such as in the case that the external processing unit is implemented in a server and data is transmitted via one or more networks or the Internet.

In a variant, as shown in FIG. 17, part of the processing is carried out in a distant server 310 to which data is transmitted via the internet for example.

EXAMPLES

Figure 10A:
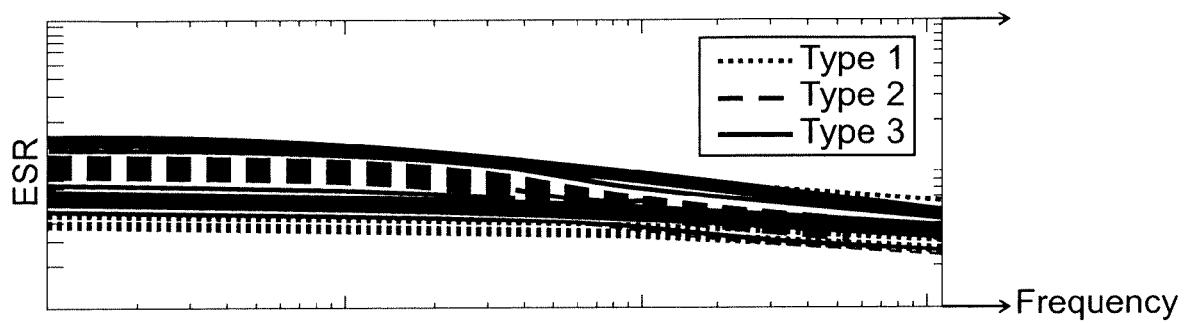
FIGS. 10A and 10B show amplitude and phase spectra for experimental data.
Figure 10B:
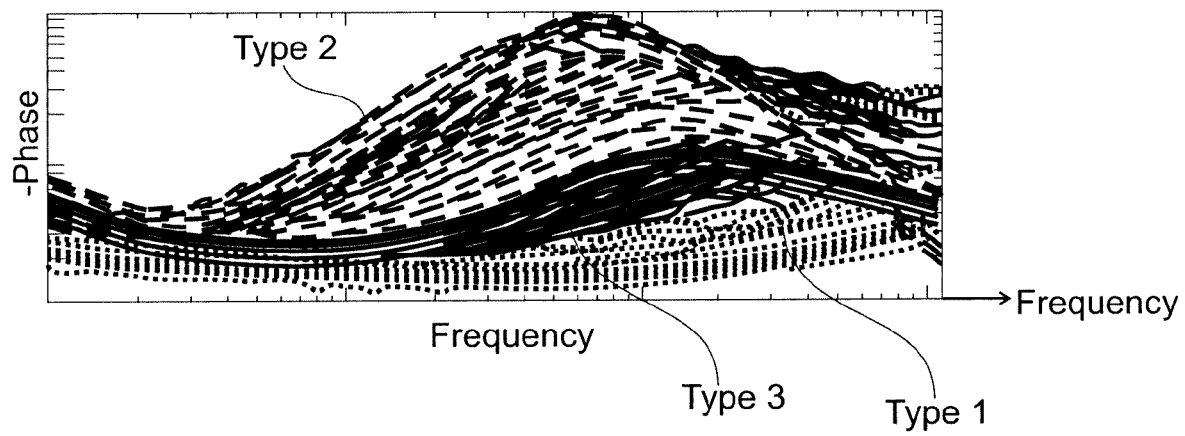

FIGS. 10A and 10B show a collection of amplitude and phase of an impedance spectra measured for cellular structures comprising respectively three cell types, i.e. platelets, smooth muscle cells and endothelial cells.

Comparative Examples

First, an equivalent circuit model without CPE is used, consisting of a double layer capacitance $C_{d1}$ in series with a solution resistance in series with a $R_0 C_{mix}$ ($R_0$ resistance in parallel with $C_{mix}$ capacitance).

Then, the $C_{mix}$ parameter describing the impact of the cells layers on the complex impedance is computed.

Figure 11A:
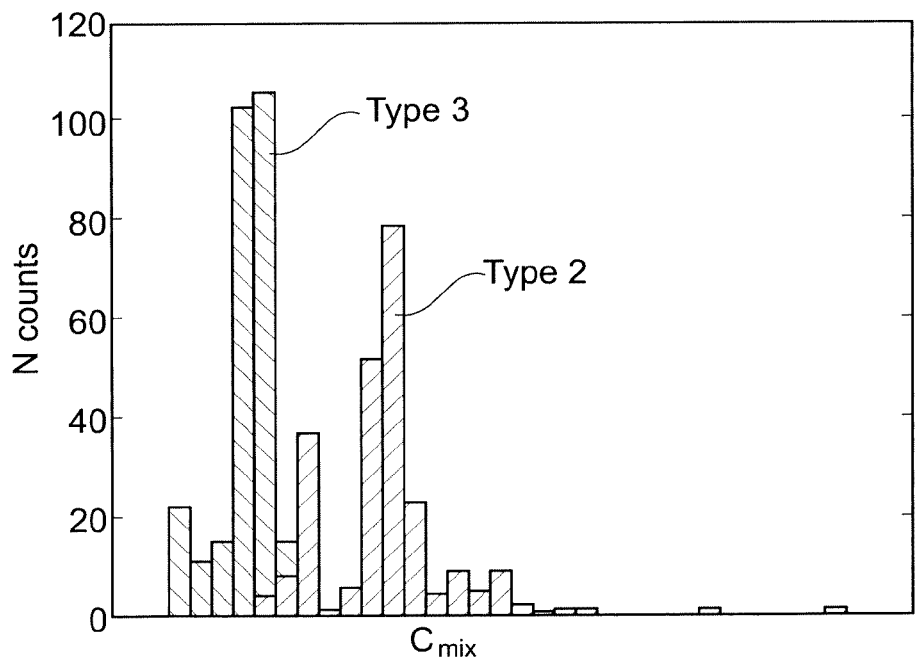
Figure 11B:
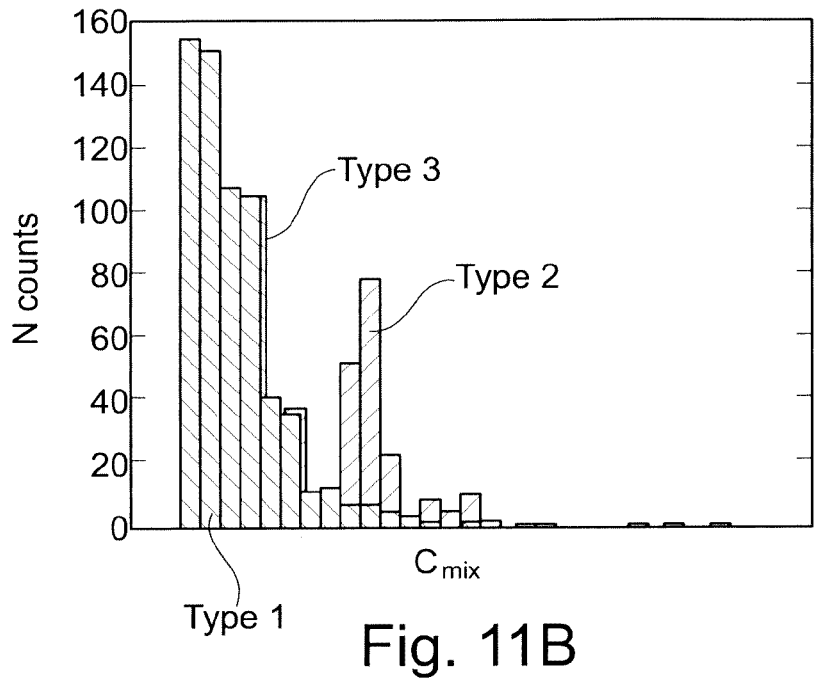

The result of the distribution of $C_{mix}$ for two cell types is shown in FIG. 11A. It is possible to distinguish between the two cell types. However, if adding a third cell type the three cell types cannot be distinguished any longer, as shown in FIG. 11B.

If one uses a more sophisticated approach and implement CPE elements into the equivalent circuit model, and uses for example the model 34 shown in FIG. 5, there are six parameters describing the system, i.e. $R_0$, $R_{inf}$, $Q_0$, $\beta$, $Q_{d1}$ and $\alpha$.

These parameters can be computed so that the impedance of the equivalent circuit model best fit the experimental impedance spectra curves of FIGS. 10A and 10B.

Then, one can display for each parameter the distribution of this parameter for the three cell types, as shown in FIGS. 12A to 12F.

One can see that for each parameter the three cell types cannot be distinguished clearly, and no linear combination of these parameters can provide the cell discrimination that is looked for.

Examples According to the Invention

FIG. 13 shows the distribution of a value representative of the effective capacitance $C_{eff}$ for the three cell types, determined based on the formula [9] above.

One can see that it is possible to clearly distinguish between all three cell types. The precision is over 90%. The differentiation between cells is significantly improved compared to FIGS. 12A-12F.

If the equivalent circuit is the one 34' of FIG. 5A, one obtains the $C_{eff}$ distribution of FIG. 14.

If one considers $R_0$-$R_{inf}$ is large in respect to $R_{inf}$, the equation [9] can be simplified as $C_{eff} = Q_0^{1/\alpha} \times R_1^{(1-\alpha)/\alpha}$ The resulting distribution of $C_{eff}$ is shown in FIG. 15. One can see that the three cell types can still be distinguished with a precision of about 85%.

The distributions shown in FIGS. 13 to 15 may serve as reference data for cell type determination.

For example, an impedance spectrum may be measured in similar conditions as the impedance spectra of FIGS. 10A and 10B, and based on this spectrum the values of parameters $R_0$, $R_{inf}$, $Q_0$, $\beta$, $Q_{d1}$ and $\alpha$ are determined. This determination may be based on least square fitting of the impedance curves of amplitude and phase with the equivalent circuit model 34 of FIG. 5.

Then, once the parameter values $R_0$, $R_{inf}$, $Q_0$ and $\alpha$ are known, the effective capacitance $C_{eff}$ can be computed and the value compared with the distribution of FIG. 13 to determine to what cell type it corresponds. For example, a low value of $C_{eff}$ in nF/cm$^2$ will indicate that the cells are of first type; a value between about 50 and about 100 that the cells are of type 3, and a value of over about 100 that the cells are of type 2.

The invention claimed is:

1. A method for discriminating cells of a cellular structure, the method comprising:
    operating a first device applied to the cellular structure within an animal to make in vivo measurements of impedance of the cellular structure contacted by the first device, wherein the first device that is applied to the cellular structure within the animal comprises a plurality of electrodes to contact the cellular structure and an internal electronic control to measure a discrete impedance spectrum of the cellular structure, wherein the internal electronic control measures the discrete impedance spectrum at least in part by applying to the cellular structure, via a first portion of the plurality of electrodes, an alternating current at multiple frequencies and calculating an impedance of the cellular structure at each of the multiple frequencies, the multiple frequencies not being continuous; and
    discriminating, with a second device, the cells of the cellular structure within the animal, wherein the discriminating comprises:
        computing, from the discrete impedance spectrum, at least one parameter that is representative of the cellular structure contacted by the plurality of electrodes;
        comparing the at least one parameter that is representative of the cellular structure to a plurality of reference values; and determining based at least on a result of the comparing, one or more items of information regarding the cellular structure.

2. The method of claim 1, wherein operating the first device to make in vivo measurements of the impedance of the cellular structure comprises operating a surgical device within the animal to make the in vivo measurements of the impedance of the cellular structure, wherein a portion of the surgical device that is disposed within the animal includes the internal electronic control.

3. The method of claim 2, wherein the surgical device is a guidewire or a catheter.

4. The method of claim 1, wherein determining the one or more items of information regarding the cellular structure comprises determining, based at least on the result of the comparing, a cellular composition of the cellular structure.

5. The method of claim 4, wherein determining the cellular composition of the cellular structure comprises determining, based at least on the result of the comparing, one or more types of cells present in the cellular structure.

6. The method of claim 4, wherein determining the cellular composition of the cellular structure comprises determining, based at least on the result of the comparing, one or more conditions of cells present in the cellular structure.

7. The method of claim 1, wherein computing the at least one parameter from the discrete impedance spectrum comprises computing an effective capacitance of the cellular structure from the discrete impedance spectrum.

8. The method of claim 1, wherein computing the at least one parameter from the discrete impedance spectrum comprises computing, from the discrete impedance spectrum, an effective capacitance of the cellular structure and at least one other parameter of the cellular structure.

9. The method of claim 1, wherein computing the at least one parameter from the discrete impedance spectrum comprises identifying, from the discrete impedance spectrum, an equivalent circuit model for the cellular structure, the equivalent circuit model including at least one constant phase element.

10. The method of claim 1, further comprising receiving the discrete impedance spectrum from the first device at the second device while the first device is disposed at least partially within the animal.

11. The method of claim 1, wherein:
the plurality of reference values are stored in a data structure together with items of information;
comparing the at least one parameter to the plurality of reference values comprises identifying at least one reference value, of the plurality of reference values, that is a match to the at least one parameter; and
determining the one or more items of information regarding the cellular structure based at least on a result of the comparing comprises retrieving from the data structure one or more items of information associated with the at least one reference value identified as a match.

12. The method of claim 11, where the plurality of reference values are values determined from testing performed on one or more tissues of known compositions, in known media, and with known test conditions.

13. A system for discriminating cells of a cellular structure, the system comprising:
a first surgical device for which at least a part is arranged to be disposed within an animal to make in vivo measurements of impedance of the cellular structure within the animal that is contacted by the part, the part of the first surgical device arranged to be disposed within the animal comprising a plurality of electrodes to contact the cellular structure and an internal electronic control to measure a discrete impedance spectrum of the cellular structure, wherein the internal electronic control measures the discrete impedance spectrum at least in part by applying to the cellular structure, via a first portion of the plurality of electrodes, an alternating current at multiple frequencies and calculating an impedance of the cellular structure at each of the multiple frequencies, the multiple frequencies not being continuous; and
a second device, arranged to be disposed outside of the animal, to receive the discrete impedance spectrum from the surgical device and to discriminate the cells of the cellular structure within the animal, wherein the discriminating comprises:
computing, from the discrete impedance spectrum, at least one parameter that is representative of the cellular structure contacted by the plurality of electrodes;
comparing the at least one parameter that is representative of the cellular structure to a plurality of reference values; and
determining, based at least on a result of the comparing, one or more items of information regarding the cellular structure.

14. The system of claim 13, wherein the second device is arranged to receive the discrete impedance spectrum from the surgical device at least partially via a wired connection.

15. The system of claim 13, wherein the surgical device is a guidewire, a catheter, or a probe.

16. The system of claim 13, wherein determining the one or more items of information regarding the cellular structure comprises determining, based at least on the result of the comparing, a cellular composition of the cellular structure and/or a number of cellular layers of the cellular structure.

17. At least one non-transitory computer-readable storage medium having encoded thereon executable instructions that, when executed by at least one processor, cause the at least one processor to carry out a method for discriminating cells of a tissue within an animal, the method comprising:
receiving, from a first surgical device disposed at least partially within the animal to make in vivo measurements of impedance of the tissue within the animal contacted by the first surgical device, at a second device, a discrete impedance spectrum of the tissue, the discrete impedance spectrum indicating impedance of the tissue at multiple frequencies, the multiple frequencies not being continuous; and
discriminating, with the second device, the cells of the tissue within the animal, wherein the discriminating comprises:
computing, from the discrete impedance spectrum, at least one parameter that is representative of the tissue contacted by the first surgical device;
comparing the at least one parameter that is representative of the tissue to a plurality of reference values for a plurality of known tissue compositions; and
determining, based at least on a result of the comparing, a composition of the tissue.

18. The at least one non-transitory computer-readable storage medium of claim 17, wherein receiving the discrete impedance spectrum from the surgical device comprises receiving the discrete impedance spectrum from a guidewire, a catheter, or a probe.

19. The at least one non-transitory computer-readable storage medium of claim 17, wherein receiving the discrete impedance spectrum from the surgical device comprises receiving the discrete impedance spectrum from a surgical device for which at least a part is arranged to be disposed within the animal to make in vivo measurements of impedance of a cellular structure within the animal that is contacted by the part, the part of the surgical device arranged to be disposed within the animal comprising a plurality of electrodes to contact the cellular structure and an internal electronic control to measure a discrete impedance spectrum of the cellular structure, wherein the internal electronic control measures the discrete impedance spectrum at least in part by applying to the cellular structure, via a first portion of the plurality of electrodes, an alternating current at multiple frequencies and calculating an impedance of the cellular structure at each of the multiple frequencies, the multiple frequencies not being continuous or pseudo-continuous.

20. The method of claim 1, wherein the multiple frequencies are not pseudo-continuous.

21. The system of claim 13, wherein the multiple frequencies are not pseudo-continuous.

22. The at least one non-transitory computer-readable storage medium of claim 17, wherein the multiple frequencies are not pseudo-continuous.

* * * * *